(12) United States Patent
Reisinger et al.

(10) Patent No.: US 9,555,189 B2
(45) Date of Patent: Jan. 31, 2017

(54) FLUID MANAGEMENT DEVICE HAVING ROTATING CAROUSEL WITH CONTAINER HOLDERS FOR VERTICALLY POSITIONING A CONTAINER DURING AUTOMATED SPIKING AND INJECTION INTO PATIENT

(75) Inventors: Claus-Peter Reisinger, Berlin (DE); Klaus Urich, Berlin (DE); Matthias Burg, Berlin (DE); Andreas Kalitzki, Berlin (DE); Samantha Anne Patterson, Cambridge (GB); Kathryn Anne Louise Farrell, Cambridge (GB); Andrew Murray Gow, Cambridge (GB); Scott Alexander Lewis, Cambridge (GB); Mark Jeffrey Edhouse, Cambridgeshire (GB)

(73) Assignee: BAYER INTELLECTUAL PROPERTY GMBH, Monheim (DE)

( * ) Notice: Subject to any disclaimer, the term of this patent is extended or adjusted under 35 U.S.C. 154(b) by 566 days.

(21) Appl. No.: 13/512,565

(22) PCT Filed: Nov. 24, 2010

(86) PCT No.: PCT/EP2010/068097
§ 371 (c)(1),
(2), (4) Date: Sep. 5, 2012

(87) PCT Pub. No.: WO2011/064240
PCT Pub. Date: Jun. 3, 2011

(65) Prior Publication Data
US 2012/0330152 A1    Dec. 27, 2012

(30) Foreign Application Priority Data
Nov. 27, 2009 (EP) ................................ 09177313

(51) Int. Cl.
*B65B 1/36* (2006.01)
*A61M 5/168* (2006.01)
(Continued)

(52) U.S. Cl.
CPC ......... *A61M 5/16827* (2013.01); *A61M 5/007* (2013.01); *A61M 5/1407* (2013.01); *A61M 5/1413* (2013.01); *A61M 5/1414* (2013.01)

(58) Field of Classification Search
CPC .... A61M 1/024; A61M 39/281; A61M 5/007; A61M 5/1407; A61M 5/16827; A61M 5/008; A61M 5/1414; B65B 5/06
(Continued)

(56) References Cited

U.S. PATENT DOCUMENTS 2,388,111 A * 10/1945 Berman .................. G01F 11/32
222/165
3,807,467 A * 4/1974 Tascher et al. ................ 141/375
(Continued)

FOREIGN PATENT DOCUMENTS

RU          40893 U1    10/2004
WO       9910027 A1     3/1999
(Continued)

OTHER PUBLICATIONS

The International Search Report and Written Opinion mailed Aug. 7, 2014 from corresponding PCT Application No. PCT/US2014/015507.
(Continued)

*Primary Examiner* — Bhisma Mehta
*Assistant Examiner* — Matthew A Engel
(74) *Attorney, Agent, or Firm* — Joseph L. Kent; David Schramm; James R. Stevenson

(57) ABSTRACT

A fluid management system adapted to automatically supply fluid for injection into a patient is disclosed. The fluid
(Continued)

management system includes a fluid management device, a fluid transfer system and a fluid injector. The fluid management device serves to store and administrate multi-dose containers. The fluid transfer system connects an outlet of these containers to the injector which withdraws a fluid from the containers via the fluid transfer system and injects the fluid to an administration device at the patient. The fluid management device includes at least one rotating carousel having a vertical axis of rotation, at least two container holders attached to the rotating carousel and adapted to position the container vertically with a septum covered end facing downwards, and a spike holder mounted below the rotating carousel and oriented so the spike holder axially aligns a spike connected to the spike holder with the axis of the container.

18 Claims, 14 Drawing Sheets

(51) Int. Cl.
  *B67B 7/04*     (2006.01)
  *A61M 5/00*    (2006.01)
  *A61M 5/14*    (2006.01)

(58) Field of Classification Search
  USPC ......... 600/431; 604/416; 141/129, 140, 144, 141/145, 151, 330; 222/160, 167, 165
  See application file for complete search history.

(56) References Cited

U.S. PATENT DOCUMENTS

| | | | | |
|---|---|---|---|---|
| 4,508,123 | A * | 4/1985 | Wyatt et al. | 600/505 |
| 4,568,345 | A * | 2/1986 | Keilman et al. | 604/403 |
| 4,595,562 | A * | 6/1986 | Liston et al. | 422/65 |
| 4,730,435 | A * | 3/1988 | Riddle et al. | 53/167 |
| 4,791,821 | A * | 12/1988 | Spencer | G01N 1/2035 141/301 |
| 4,842,028 | A * | 6/1989 | Kaufman | A61J 1/20 141/10 |
| 4,879,915 | A * | 11/1989 | Spencer | G01N 1/2035 141/330 |
| 5,109,894 | A * | 5/1992 | McGregor | 141/83 |
| 5,229,074 | A * | 7/1993 | Heath et al. | 422/64 |
| 5,451,528 | A * | 9/1995 | Raymoure et al. | 436/533 |
| 5,479,969 | A * | 1/1996 | Hardie et al. | 141/130 |
| 5,502,944 | A * | 4/1996 | Kraft et al. | 53/55 |
| 5,522,512 | A * | 6/1996 | Archer et al. | 209/580 |
| 5,902,298 | A * | 5/1999 | Niedospial et al. | 604/414 |
| 5,911,252 | A * | 6/1999 | Cassel | 141/234 |
| 5,921,419 | A * | 7/1999 | Niedospial et al. | 215/247 |
| 5,935,523 | A * | 8/1999 | McCandless | G01N 35/1079 141/330 |
| 5,968,014 | A * | 10/1999 | Neftel et al. | 604/151 |
| 6,006,946 | A * | 12/1999 | Williams et al. | 221/9 |
| 6,037,598 | A * | 3/2000 | Cicha | 250/455.11 |
| 6,096,561 | A * | 8/2000 | Tayi | 436/518 |
| 6,148,877 | A * | 11/2000 | Bethke | 141/103 |
| 6,360,794 | B1 * | 3/2002 | Turner | 141/329 |
| 6,375,624 | B1 * | 4/2002 | Uber et al. | 600/549 |
| 6,418,877 | B1 | 7/2002 | Fredericks et al. | |
| 6,436,349 | B1 * | 8/2002 | Carey et al. | 422/64 |
| 6,498,037 | B1 * | 12/2002 | Carey et al. | 436/50 |
| 6,604,903 | B2 * | 8/2003 | Osborne et al. | 414/411 |
| 6,616,771 | B2 * | 9/2003 | Osborne et al. | 134/18 |
| 6,877,530 | B2 * | 4/2005 | Osborne | B65B 7/2821 141/198 |
| 7,017,623 | B2 * | 3/2006 | Tribble | G09F 3/02 141/104 |
| 7,128,105 | B2 * | 10/2006 | Tribble et al. | 141/319 |
| 7,240,699 | B2 * | 7/2007 | Osborne | B65B 7/2821 141/104 |
| 7,610,115 | B2 * | 10/2009 | Rob | A61J 1/20 318/568.11 |
| 7,662,124 | B2 * | 2/2010 | Duchon et al. | 604/19 |
| 7,728,711 | B2 * | 6/2010 | Shoenfeld | 340/5.73 |
| 7,814,731 | B2 * | 10/2010 | Bender et al. | 53/467 |
| 7,900,658 | B2 * | 3/2011 | Osborne | A61J 1/20 141/104 |
| 7,931,859 | B2 * | 4/2011 | Mlodzinski et al. | 422/24 |
| 8,267,129 | B2 * | 9/2012 | Doherty | A61J 1/2096 141/1 |
| 8,286,671 | B1 * | 10/2012 | Strangis | B65B 7/28 141/104 |
| 8,386,070 | B2 * | 2/2013 | Eliuk et al. | 700/214 |
| 8,539,989 | B2 * | 9/2013 | Giribona et al. | 141/91 |
| 8,580,574 | B2 * | 11/2013 | Smith | 436/180 |
| 8,807,177 | B2 * | 8/2014 | Strangis | 141/9 |
| 2003/0229309 | A1 * | 12/2003 | Babkes et al. | 604/131 |
| 2005/0045242 | A1 * | 3/2005 | Osborne | 141/27 |
| 2005/0119604 | A1 | 6/2005 | Bonney et al. | |
| 2005/0137524 | A1 * | 6/2005 | Sakal et al. | 604/93.01 |
| 2005/0203329 | A1 * | 9/2005 | Muto et al. | 600/1 |
| 2005/0224137 | A1 * | 10/2005 | Tribble et al. | 141/329 |
| 2005/0252574 | A1 * | 11/2005 | Khan et al. | 141/198 |
| 2005/0278066 | A1 * | 12/2005 | Graves | G21F 5/015 700/239 |
| 2006/0081305 | A1 * | 4/2006 | Monti | B65B 3/323 141/144 |
| 2007/0110637 | A1 * | 5/2007 | Phelps | B01J 19/0046 422/130 |
| 2007/0140925 | A1 * | 6/2007 | Phelps | B01J 19/0046 422/130 |
| 2008/0004576 | A1 * | 1/2008 | Tanaka et al. | 604/317 |
| 2008/0081000 | A1 * | 4/2008 | MacLeod et al. | 422/68.1 |
| 2008/0114328 | A1 * | 5/2008 | Doherty et al. | 604/414 |
| 2008/0147014 | A1 * | 6/2008 | Lafferty | 604/191 |
| 2008/0211674 | A1 * | 9/2008 | Gibson et al. | 340/572.1 |
| 2009/0198208 | A1 * | 8/2009 | Stavsky et al. | 604/407 |
| 2009/0280572 | A1 * | 11/2009 | Ribeiro | G01N 35/025 436/164 |
| 2009/0281460 | A1 | 11/2009 | Lowery et al. | |
| 2010/0217154 | A1 * | 8/2010 | Deshmukh et al. | 600/575 |
| 2011/0307117 | A1 * | 12/2011 | McKinnon et al. | 700/300 |
| 2012/0330152 | A1 * | 12/2012 | Reisinger | A61M 5/007 600/431 |
| 2013/0340795 | A1 * | 12/2013 | Gaskill-Fox | G01N 11/02 134/26 |

FOREIGN PATENT DOCUMENTS

| | | |
|---|---|---|
| WO | 2004091688 A2 | 10/2004 |
| WO | 2006083359 A2 | 8/2006 |
| WO | 2007033103 A1 | 3/2007 |
| WO | 2008076631 A2 | 6/2008 |

OTHER PUBLICATIONS

International Search Report for counterpart International Patent Application No. PCT/EP2010/068097 mailed on May 19, 2011.
International Preliminary Report on Patentability and Written Opinion for counterpart International Patent Application No. PCT/EP2010/068097 issued on May 30, 2012.
RU40893U1—Machine Translation of Abstract, Published Oct. 10, 2004.

* cited by examiner

FLUID MANAGEMENT DEVICE HAVING ROTATING CAROUSEL WITH CONTAINER HOLDERS FOR VERTICALLY POSITIONING A CONTAINER DURING AUTOMATED SPIKING AND INJECTION INTO PATIENT

This application is a U.S. National Phase of International Patent Application No. PCT/EP2010/068097, entitled "Fluid Management System", filed Nov. 24, 2010, which claims priority to European Patent Application No. 09177313.5, filed Nov. 27, 2009, the disclosures of which are incorporated herein by reference in their entirety.

The present disclosure relates generally to a fluid management system (FMS) and method for the administration of fluid to a patient from multiple dose containers. The FMS presented in this disclosure is adapted to automatically supply fluid for injection into a patient.

BACKGROUND

In many medical environments, a medical fluid is injected into a patient during diagnosis or treatment. One example is the injection of contrast media into a patient to improve imaging by a diagnostic imaging procedure such as computed tomography (CT), angiographic, magnetic resonance (MR) or ultrasound imaging using a powered fluid injection system.

Various manual and automated injection systems used for performing the above-referenced procedures are known in the art. In the system as disclosed in WO 2004/091688 A2 or WO 2007/033103 A1 the containers from which the fluid for injection is withdrawn have to be prepared for use manually, i.e. manually spiked and manually mounted in withdrawal position after spiking.

A typical procedure how contrast media is prepared, handled, and administered from a multi dose container is described in the following:

The multi dose containers with contrast media are pre-warmed before use via a heater normally positioned near to the diagnostic imaging instrument. Temperature of the heater is set to 37 degrees Celsius the regular body temperature. A container with contrast media is then removed from the heater by a technician. The plastic safety cap is removed from the end of the multi dose containers to expose the rubber seal. A vented spike is connected to the contrast media injector and then manually driven into the rubber seal on the multi dose container by the technician in order to feed the injector line. Due to contamination reasons the spike has to be replaced approximately every 6-8 hours. The multi dose container is then placed in a container holder suspended from an IV pole in a vertical orientation with the container neck end facing downwards. The previously described steps are then repeated for one container of saline. The technician then draws the required contrast media and saline from the multi dose containers into the injector reservoirs via the injector user interface. Protective packaging from a new patient connection tube with cannula connection is removed. A cap used to plug the connector of the injector patient supply line is manually removed. The patient connection tube and patient supply line are connected via cannula connection. Air is then expelled from the tubes by the technician manually activating the injector which then pumps both saline and contrast media into a bin. The technician examines the tubes by eye to ascertain when the lines are purged and subsequently ceases the injector pump. The packaging from a new cannula connector is then removed and the connector attached to the end of the patient tube.

The manual procedure described above is costly and not very efficient, such that it is an object of the present disclosure to achieve a higher degree of automation. The multiple drug injection apparatus disclosed in WO 2008/076631 A2 shows a somewhat higher degree of automation.

However a mere automation poses additional problems. With a multi-dose-container it is always an issue that the container is used beyond the recommended in-use time or that the containers, which had been de-spiked before, are re-used.

Therefore it is desirable to have a fluid management system that is safe and efficacious to use. In particular, it is desirable to have a system accurately and precisely control the fluid containers and the withdrawal of fluid. It is also essential that the fluid supply remains contamination-free during the whole in-use time of a container.

In addition, it is desirable to have a fluid management system that is capable of using a variety of fluids, such as contrast media, saline, flushing fluids and of container sizes.

SUMMARY

In view of the foregoing, it is an object of the present disclosure to provide a fluid management system (FMS) that addresses the obstacles and disadvantages associated with conventional fluid injection practices.

The FMS according to the present disclosure is adapted to automatically supply fluid for injection into a patient. The FMS according to the disclosure comprises a fluid management device (FMD), a fluid transfer system (FTS) and an injector.

The FMD serves to store and administrate fluid from multi dose containers, although it is also possible to store and administrate fluid from single dose containers. The term "container" shall be understood to include also at least a bottle, a pouch, a bag, a cartridge or carpule. The FTS connects the outlet of the containers stored within the FMD to the injector and the injector withdraws the fluid via FTS from the containers and injects the fluid to an administration device at the patient. The injector comprises at least one pump and is programmed to inject a predetermined amount of fluid with predetermined flow rate.

The FMD comprises at least a rotating carousel with the axis of rotation being vertical, at least two container holders attached to the rotating carousel, said container holders being adapted to position a container vertically with the open end of the neck facing downwards and a spike holder mounted below the rotating carousel and oriented such that the spike holder would axially align a spike connected to the spike holder with the axis of the container loaded into the container holder and being in spiking position.

In one embodiment the FMD comprises two rotating carousels. In another embodiment the FMD comprises further one or more, preferably two, container holders not being attached to the rotating carousel.

Preferably each rotating carousel is mounted in a separate chamber and each container holder not being attached to the rotating carousel is also mounted in a separate chamber. In one embodiment the FMD has a chassis framework to which the one or more chambers are mounted.

Preferably the rotating carousel has a carousel drive shaft positioned at the axis of rotation.

A plate may be attached to the drive shaft to which the container holders are mounted vertically.

In one embodiment up to ten container holders may be attached to the rotating carousel, preferably five container holders are attached to the rotating carousel. All container holders attached to the same rotating carousel may be adapted to hold containers of equal size. Alternatively some container holders may be adapted to hold containers of different size than other container holders. Preferably one container holder is adapted to hold a container that is smaller in size than the other containers.

Preferably the container holders are equally spaced on a circle around the axis of rotation.

At least one chamber, preferably the chambers with the rotating carousel, may be temperature-controlled.

Preferably each chamber can be accessed by an individual hinged lid or door. Such lid or door may be transparent or include a window for visual inspection of each chamber's content The FMD may further comprise for each rotating carousel a carousel drive system having a motor, and means to transmit rotation from the motor axis to the shaft of the rotating carousel. Preferably the FMD further comprises means to disengage the shaft of the rotating carousel from the motor axis in case the lid or door of the chamber housing said rotating carousel is being opened.

Each spike holder may be moveably mounted to a linear slide allowing the spike holder to slide in vertical direction. The FMD may further comprise for each spike holder an automated spiking system having a motor and means to move the spike holder mounted in the linear slide.

The FMD may further comprise a central electronic control system (CECS) to control the carousel drive system and the automated spiking system. Further the CECS may be in communication with and adapted to monitor/control
 a. information output device such as a display
 b. user input device like touch screen or keyboard
 c. temperature in temperature-controlled chambers
 d. fluid level sensors
 e. position control sensors for spike
 f. position control sensors for rotating carousel
 g. valves in FTS tubing
 h. 2-way data transfer system for communication with the CM injector and/or a computer network
 i. 1-way data transfer system such as a reader for reading data from data storages on containers or fluid transfer systems (FTSs)
 j. data storage The fluid transfer system comprises a first transfer tubing with at least two first ends, each of the first ends connected to a spike, and at least two second ends, each second end corresponding to a first end; a manifold having at least two input openings and one output opening, the second ends of the transfer tubing being connected to the input openings of the manifold; a second transfer tubing being connected to the output opening of the manifold with its first end; and a valve mounted between each first end and second end of the first transfer tubing. By means of the valves fluid can be extracted selectively from one of the spiked containers.

The second end of the second transfer tubing may be adapted to be connected to an injector The fluid transfer system may further comprise data storage means for storing a unique identifier of the fluid transfer system. In reading the unique identifier the CECS can log the use of a specific fluid transfer system and alert the user via information output device if the maximum in-use time for a spike has been reached.

The base of the spike includes seating and attachment means to connect the spike to corresponding seating and attachment means at the spike holder of the FMD. The top of the spike is adapted to enter into a container septum. To allow fluid to be easily withdrawn through the spike a vented spike is preferred. The spike may be covered by a sheath prior use to avoid contamination.

The present disclosure is further directed to a method for automatic supply of fluid for injection into a patient comprising
 providing a fluid management device adapted to house at least one container with fluid in a vertical position with the open end of the neck facing downwards and having a spike holder mounted and oriented such that the spike holder would axially align a spike connected to the spike holder with the axis of the container loaded in the container holder and being in spiking position;
 providing a fluid transfer system having a transfer tubing with a first end connected to a spike and a second end adapted to be connected to an injector;
 loading at least one container with the open end of the neck facing downwards into the fluid management device, said open end of the neck being covered by a septum;
 attaching the spike to the spike holder and the second end of the transfer tubing to an injector;
 moving the spike into the septum;
 withdrawing fluid from the container.

The method further comprises withdrawing the spike from the septum of the container. The withdrawal of the spike from the septum may occur in response to a signal that was triggered because either the container is empty or the maximum in-use time for the container has been reached or the maximum in-use time for the spike has been reached. Such maximum in-use times are logged by a timer connected to the central electronic control system (CECS) of the fluid management device. The fluid level/volume of the spiked container can be monitored by the CECS via according fluid level/volume sensors.

In another embodiment at least two containers are loaded into the fluid management device. The fluid management device further has means to position subsequently each of the containers in axial alignment with the spike holder. The method further comprises moving a second container in a position where it is in axial alignment with the spike holder and moving the spike into the septum of the second container and withdrawal of fluid from the second container.

BRIEF DESCRIPTION OF THE DRAWINGS

The features of the described embodiments are specifically set forth in the appended claims. However, embodiments relating to both structure and method of operation are best understood by referring to the following description and accompanying drawings, in which similar parts are identified by like reference numerals.

DETAILED DESCRIPTION

Figure 1:
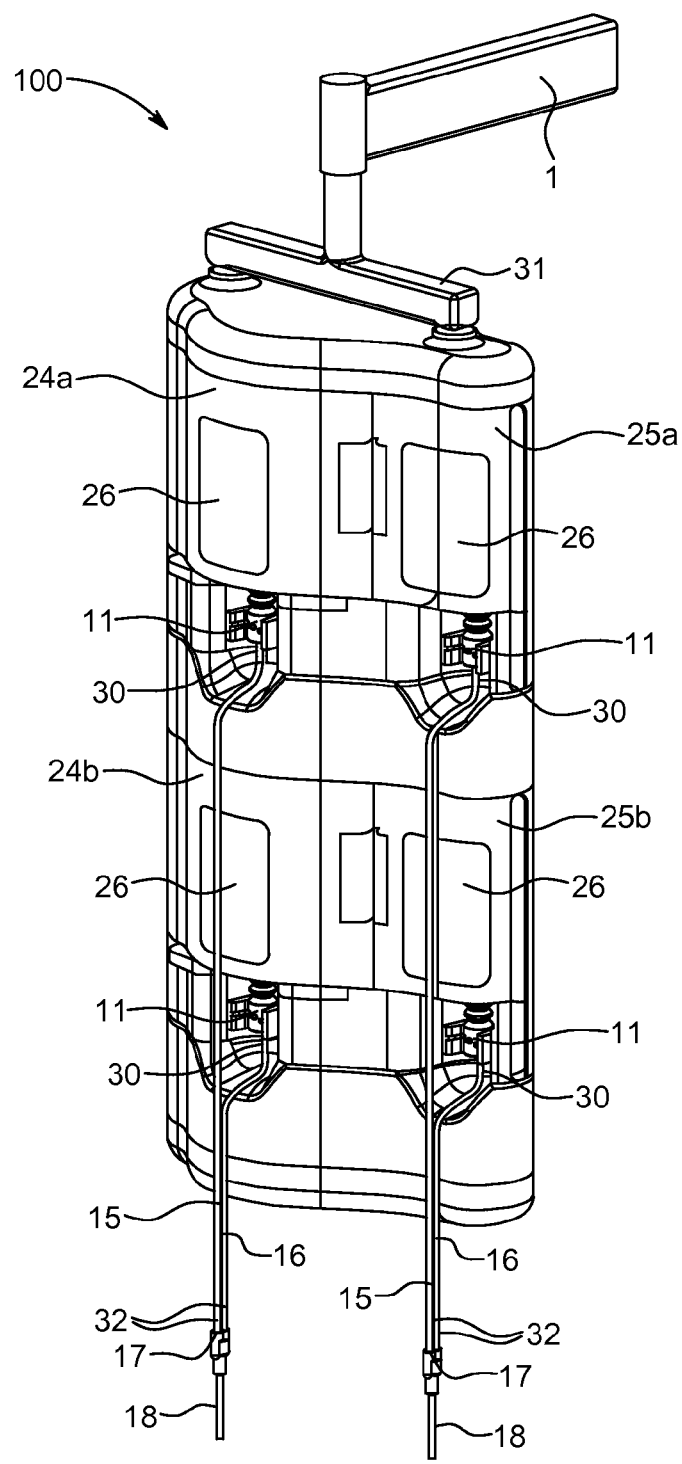
FIG. 1 is a first perspective view of a fluid management device
Figure 2:
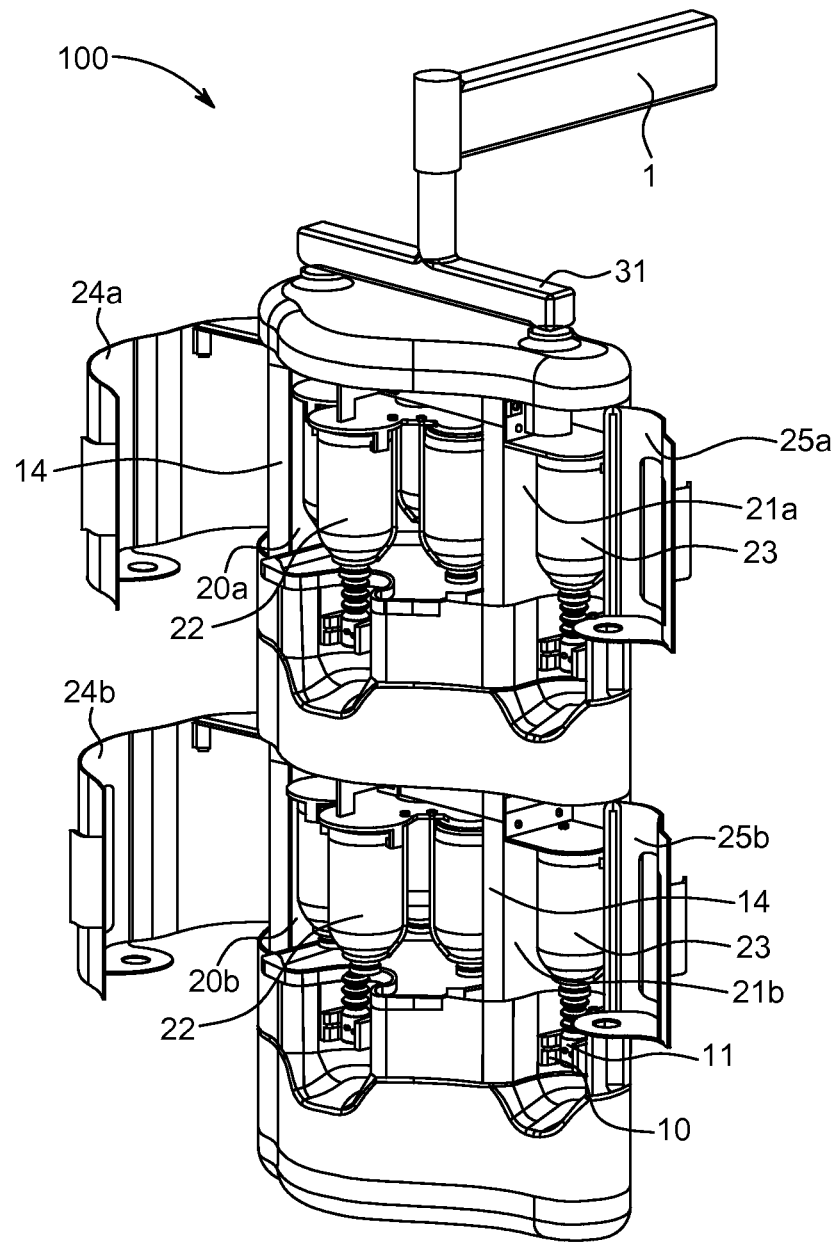
FIG. 2 is a second perspective view of a fluid management device
Figure 3:
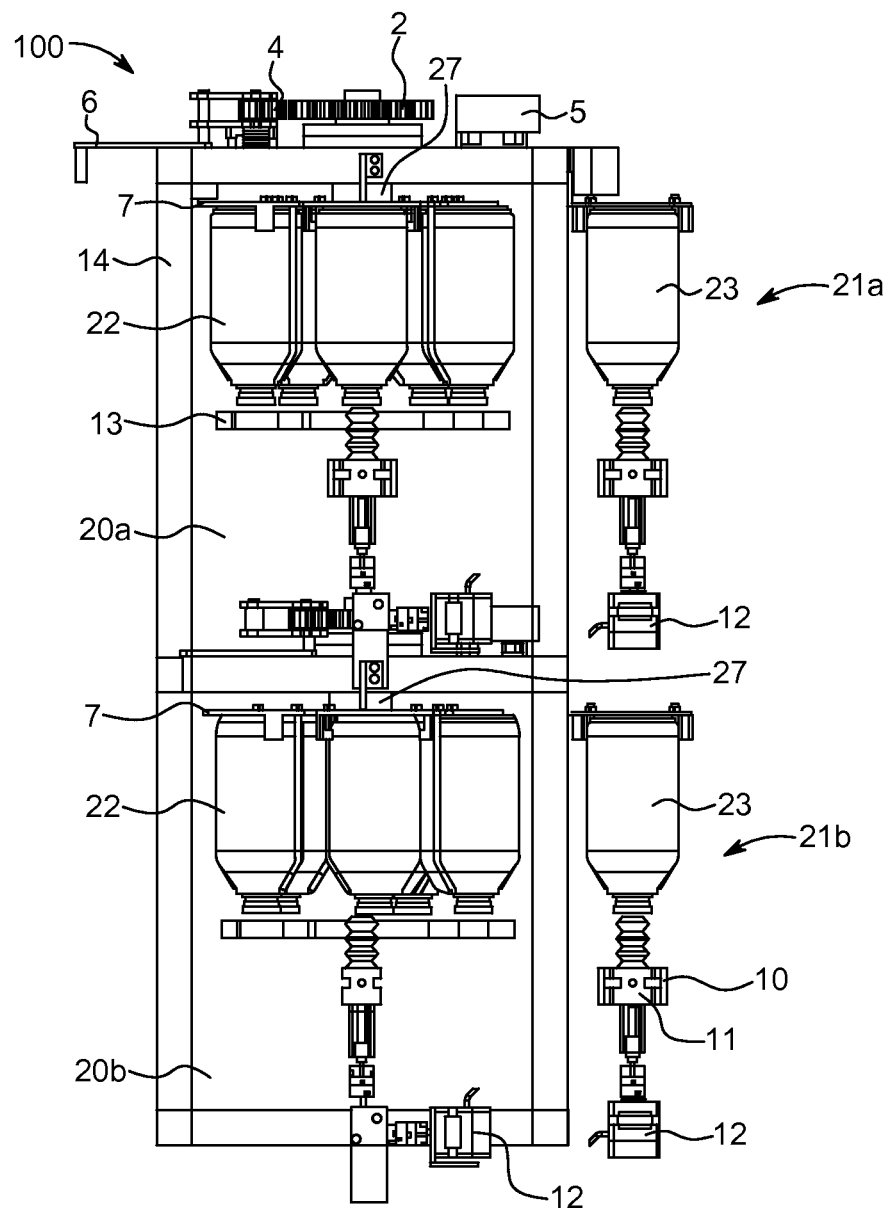
FIG. 3 is a front view of the inside of the fluid management device

The FMS according to the first exemplary embodiment described herein is adapted to automatically supply preheated contrast media (CM) and non-heated saline to a CM injector for injection into a patient from a container filled with CM (CM container) or a container filled with saline (Saline container).

According to this embodiment the fluid management device (FMD) 100 shown in FIGS. 1 to 4 consists of four separate chambers 20a, 20b, 21a, 21b. The chambers 20a and 20b are temperature-controlled and designated to house CM containers 22. The chambers 20a and 20b are positioned vertically on top of one another and are mounted to a chassis framework 14. The chambers 21a and 21b are non-temperature-controlled and designated to house Saline containers. The chambers 21a and 21b are also mounted vertically on top of each other and attached to the chassis framework 14, adjacent to the two temperature-controlled chambers 20a, 20b. The FMD 100 is encased in plastic mouldings to shield the internal components from the ambient environment. Access to each chamber 20a, 20b, 21a, 21b is provided by an individual hinged door 24a, 24b, 25a, 25b with transparent viewing window for visual inspection of each chamber's contents.

The central electronic control system (CECS) (not shown) is located in the midsection of the FMD 100 between the two vertically mounted temperature-controlled chambers 20a, 20b and attached to the chassis framework 14.

Figure 12:
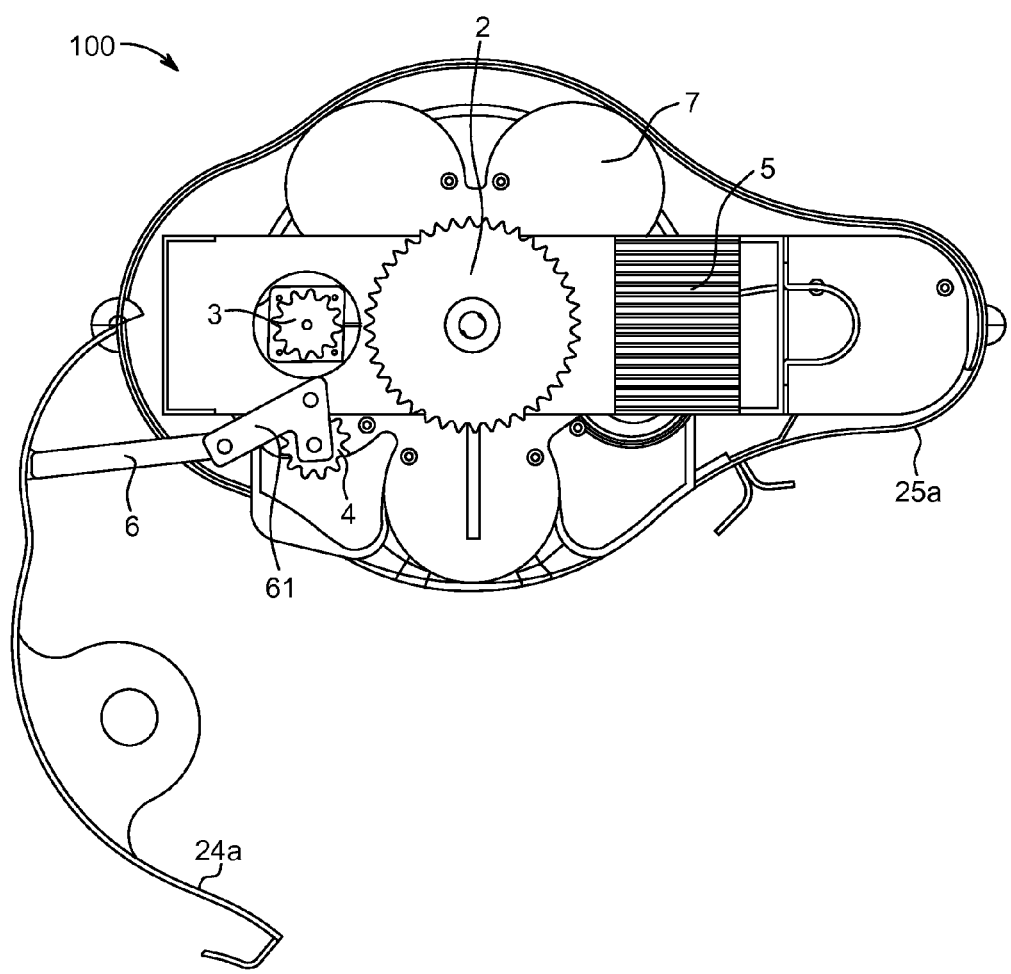
FIG. 12 is a second top view of a fluid management device
Figure 13:
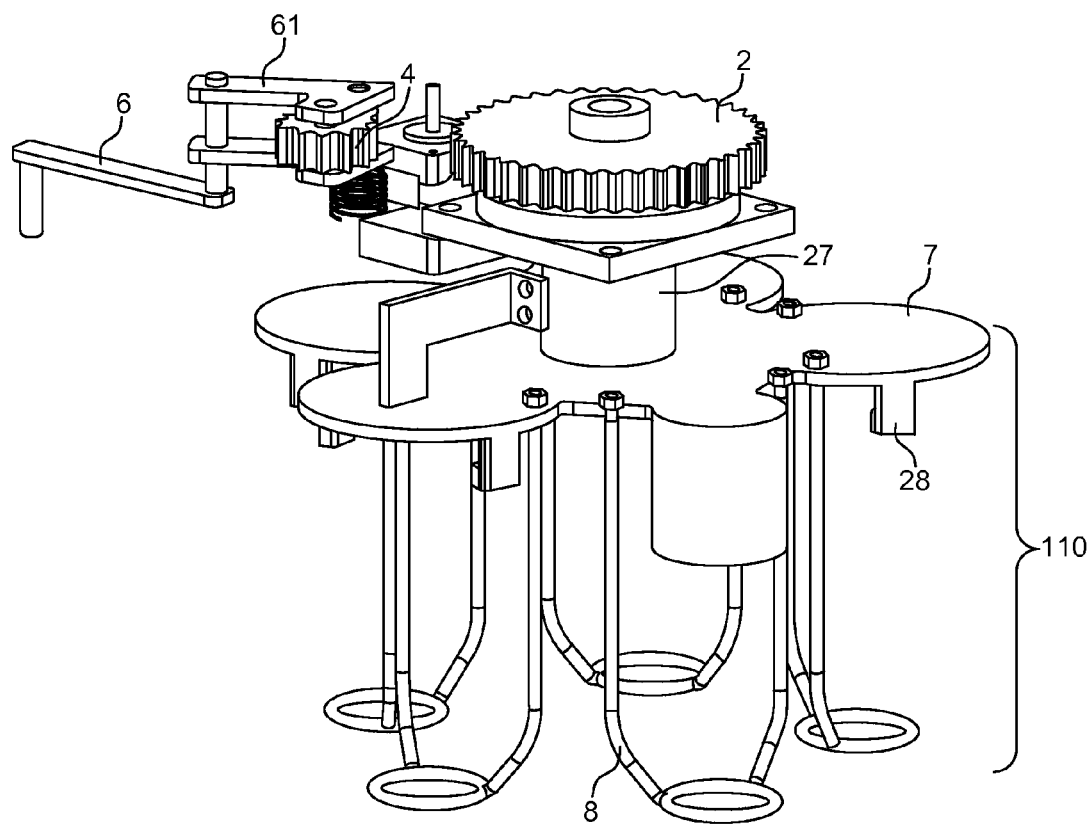
FIG. 13 is a perspective view of the rotating carousel
Figure 14:
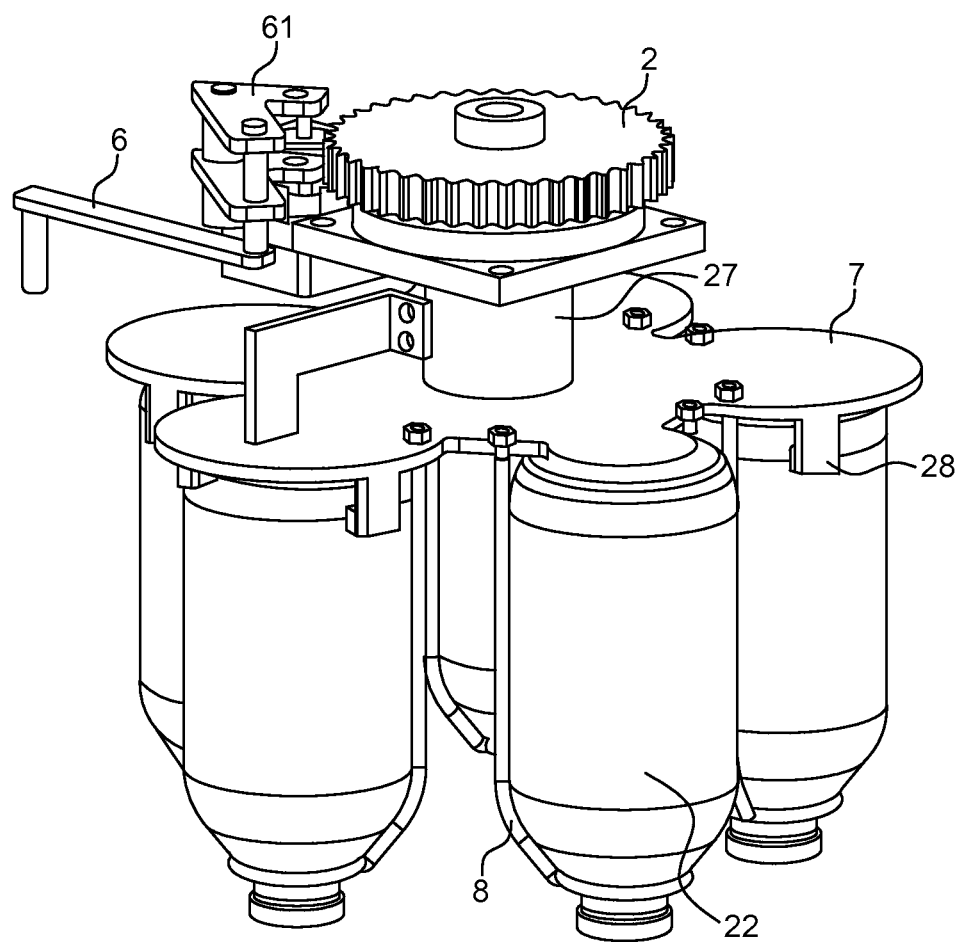
FIG. 14 is a perspective view of the rotating carousel with containers attached

A rotating carousel shown in detail in FIGS. 13 and 14 is secured within each temperature-controlled chamber 20a, 20b with the carousel drive shaft 27 positioned vertically. The carousel drive shaft 27 is mounted axially to a bearing, said bearing being securely mounted to the chassis framework 14. A carousel drive system is mounted and positioned in such a fashion as to be able to rotate the rotating carousel via the central electronic control system (CECS). The carousel drive system comprises of a motor, reduction gearbox, and supplementary running gear (spur gears, belts, etc), of which the main gear 2, the motor gear 3 and idler gear 4 can be seen best in FIGS. 4, 11 and 12.

Within each temperature-controlled chamber 20a, 20b are container holders 110 for each of five CM containers 22 (shown in detail in FIGS. 13 and 14), in order to position, orientate, and secure them such that they can be correctly axially aligned with the spike holder 10 of the automated spiking system. Each CM container holder 110 is equally spaced from the adjacent CM container holder 110 on a circle around the carousel drive shaft 27 and vertically mounted to a plate 7 with said plate 7 being attached to the carousel drive shaft 27. Each container holder 110 comprises of two clips 28 and a wire container rack 8.

Figure 4:
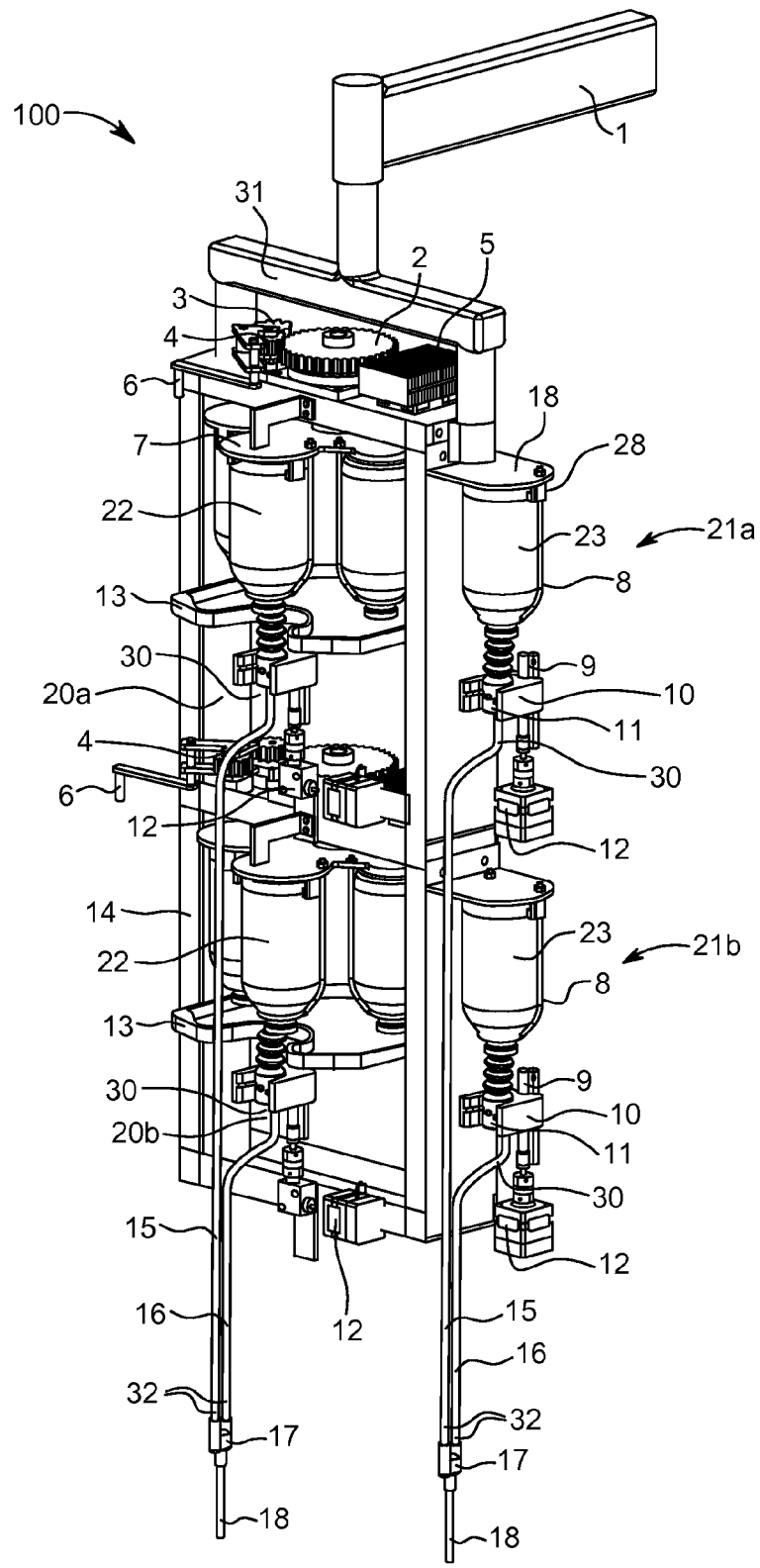
FIG. 4 is a perspective view of the inside of the fluid management device

Within each non-temperature-controlled chamber 21a, 21b is a container holder in order to position, orientate, and secure the Saline container 23 such that it can be correctly axially aligned with the spike holder 10 of the automated spiking system (see for example FIG. 4). The container holder is vertically mounted to a plate 18 with said plate 18 being attached to the chassis framework 14. Each container holder comprises of two clips 28 and a wire container rack 8

Figure 9:
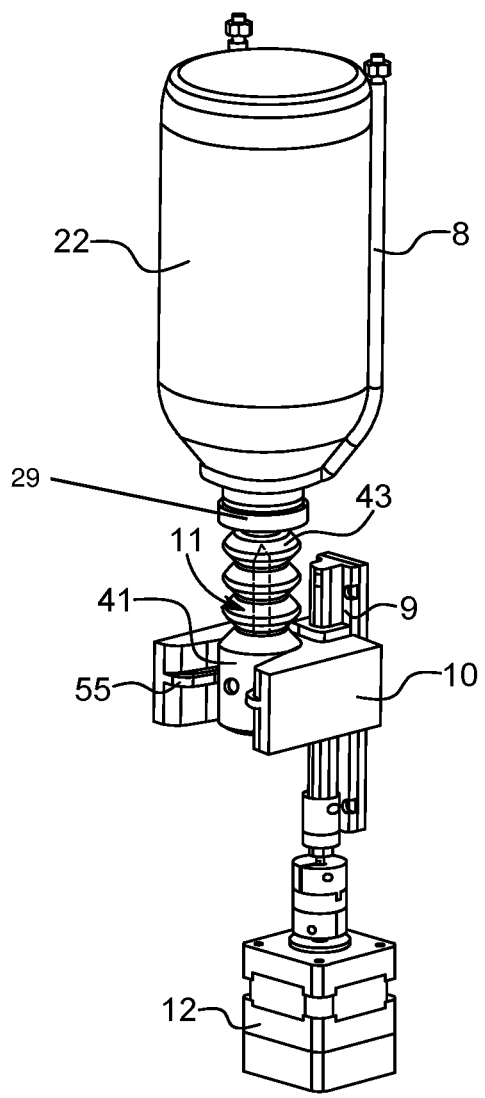
FIG. 9 is a perspective view of a spiked container and the spiking system
Figure 10:
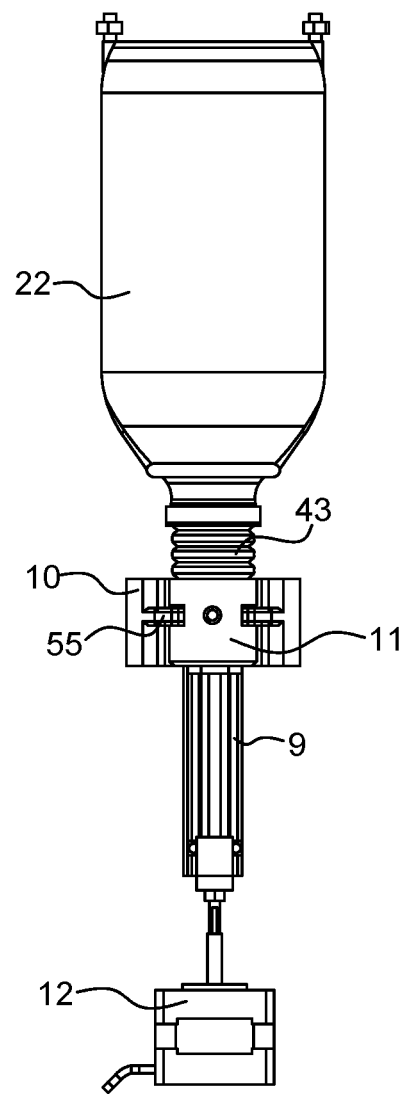
FIG. 10 is a first view of a spiked container and the spiking system

The automated spiking system as shown in more detail in FIGS. 9 and 10 comprises a spike holder 10, a linear slide 9 for the spike holder 10 and a spike drive system 12 including a motor, reduction gearbox, lead screw. The linear slide 9 with the spike holder 10 is mounted vertically to the chassis framework 14 below each of the four chambers 20a, 20b and 21a, 21b. Said automated spiking system is positioned and orientated such that the spike holder 10 is adapted to axially align a spike 11 with the axis of the container 22, 23 that is to be spiked.

A bail 31 is mounted to the chassis framework 14 to enable the FMD 100 to be mounted to a ceiling attachment arm 1.

Figure 5:
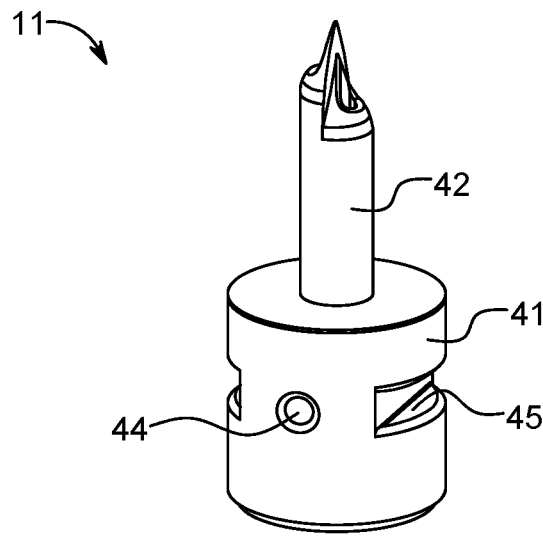
FIG. 5 is a perspective view of the spike
Figure 6:
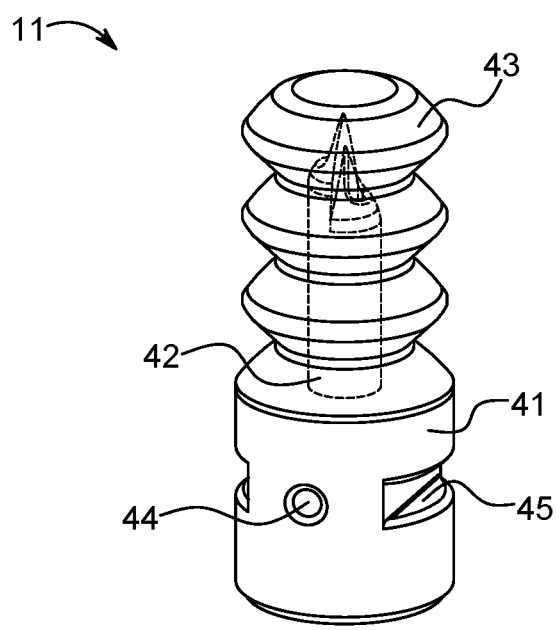
FIG. 6 is a perspective view of the spike with sheath
Figure 7:
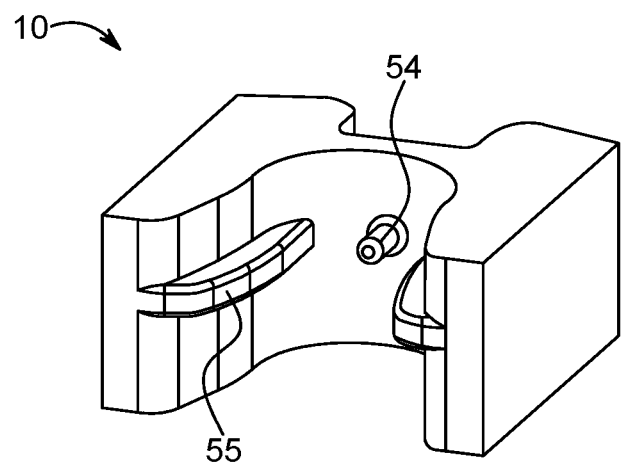
FIG. 7 is a perspective view of the spike holder
Figure 8:
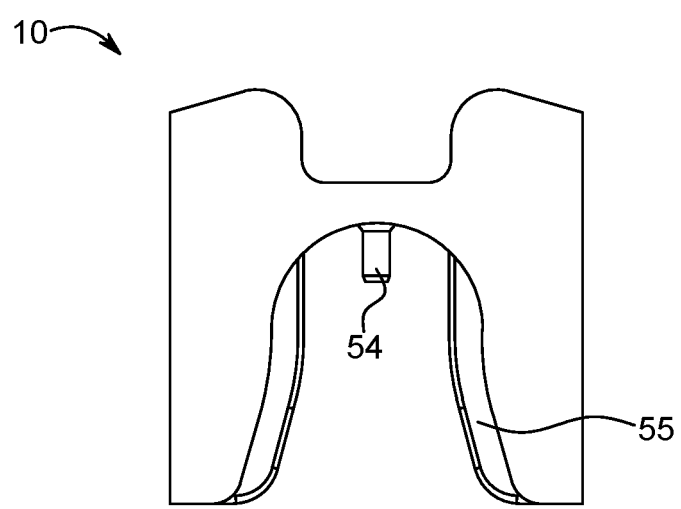
FIG. 8 is a top view of the spike holder

The fluid transfer system (FTS) as shown in FIGS. 1 and 4 includes a spike 11 for each chamber adapted to be slotted in the spike holder 10 below the chamber. The spike 11 shown in FIGS. 5 and 6 has a base 41 and a top 42. The spike 11 is a vented spike. The base 41 has two guide notches 45 on opposite sides which are adapted to hold to corresponding slide rails 55 of the spike holder 10 (see FIGS. 7 and 8). The hole 44 in the base is adapted to mount pin 54 of the spike holder 10, when the spike 11 is slotted in the spike holder 10. The spike 11 preferably has a sheath 43 to avoid contamination prior use. The FTS further comprises fluid transfer tubing 15, 16 connected to each spike 11 at a first end 30 of each tubing 15, 16 and adapted to transfer the fluid from the spiked container to the CM injector (see FIGS. 1 and 4). A Y-connector 17 is mounted between the tubing 15 of spike 11 of the top temperature-controlled chamber 20a at a second end 32 of tubing 15 and tubing 16 of spike 11 of the bottom temperature-controlled chamber 20b at a second end 32 of tubing 16. A Y-connector 17 is mounted between the tubing 15 of spike 11 of the top non-temperature-controlled chamber 21a at a second end 32 of tubing 15 and tubing 16 of spike 11 of the bottom non-temperature-controlled chamber 21b at a second end 32 of tubing 16. Tubing 18 connects the output end of the Y-connector 17 with the connector plug of the CM injector. Valves (not shown) are mounted between each spike 11 and the Y-connector 17 to control the fluid from the respective spiked container to the Y-connector. By means of the valve fluid can be extracted selectively by the CM injector from the spiked top or bottom container filled with CM or saline.

A central electronic control system (CECS) with proprietary software is used to communicate with sensors and control units of the FMD as further described below. The CECS may also be connected to a user-device interface for output of information to a user or for receiving input from a user. Especially the CECS is adapted to communicate and subsequently drive the rotating carousel and the automated spiking system of all chambers. The CECS may also allow for data storage, 1-way data transfer between data storage means on approved containers and approved FTSs and 2-way data transfer with an approved CM injector.

Preheating of the CM containers to approximately 37 degrees Celsius within each temperature-controlled chamber of the FMD is achieved through forced convection and an internal temperature control system i.e. ambient temperature of each temperature-controlled chamber is autonomously controlled. This feature negates the user having to warm a CM container before injection of the CM into the patient. In a preferred embodiment the temperature control mechanism is adapted to automatically switch on for advanced start-up before treatments begin at the start of the day.

Storage of up to five CM containers in each of the temperature-controlled chambers enables the FMD to service patients up to approximately 1 full day of treatment. The CM containers (and also the Saline containers) may have various sizes. The container holders are adapted to the size of the containers to be used therewith. Preferably 4 CM containers filled with 500 ml CM and 1 container filled with 100 ml CM are mounted within each temperature-controlled chamber. Access to one smaller sized CM container negates unnecessary wastage of CM fluid at the end the working day or between pauses in treatment of longer than the recommended in-use time for the CM containers. After spiking the CM container the CM fluid stored therein has a limited useful life, which leads to a recommended in-use time which is typically approximately 10 hours for established CMs. Therefore, if a new 500 ml CM container were used for the final treatment of the day the remaining fluid would have to be scrapped before the next morning. The ability to more efficiently control wastage of CM fluid is expedient. Storage of a Saline container filled with 500 ml saline in each of the non-temperature-controlled chambers allows up to approximately half a day of treatment supply.

The storage of multiple containers filled with CM or saline negates the user having to constantly replenish a fluid supply to the CM injector throughout the day.

In order for the FMD to supply CM and saline fluids to the CM injector, spike 11 of the FTS is inserted into the septum 29 of the respective container. To achieve this, the user must fit the spike 11 of an FTS to the spike holder 10 on the FMD 100 via a seating and attachment feature (guide notch 45, slide rail 55, pin 54, hole 44). The spike holder 10 is designed such that good axial alignment of the spike 11 with respect to the container septum 29 is achieved. Once the FMS is initialized, the containers are replenished in the chambers, and the temperature-controlled chambers are up to temperature, the central electronic control system (CECS) communicates with the automated spiking system 12 to drive the spike holder 10 with spike 11 vertically upwards, such that the spike enters through an entry point into the relevant chamber and up into the container septum 29. As this occurs, the silicone rubber bellowed sheath 43 is crushed to allow the spike top 42 full entry into the container septum 29. Using position control sensors, the CECS drives the spike 11 into the container septum 29 a prescribed distance. Once this prescribed distance has been reached the CECS deactivates the automated spiking system 12 to maintain the spike holder 10 at a set vertical location with respect to the container septum 29.

The fluid level or fluid volume within each of the spiked containers is monitored via sensors with feedback to the CECS. Once a container is emptied to a prescribed level termed "Empty", the CECS communicates with the automated spiking system 12 in order to drive the spike holder 10 vertically downward, thereby de-spiking the relevant container. This location of the container holder 8 is then marked "Empty" by the CECS. By logging the empty/full-status of the containers, the CECS can signal to the user via user-device interface, for example when the last container in a CM chamber is being spiked or when all containers in a chamber are empty.

The FMD also incorporates a push button which allows the user to over-ride the automated spiking feature in order to stop the system from spiking another container. Furthermore, it allows for a function that permits the user to manually select a small CM container for end of day treatments in order to minimise CM fluid wastage.

Automation of the rotation of the rotating carousel within each temperature-controlled chamber is used to index new CM containers so that they can be accessed and spiked. The CECS is used to drive a geared motor which in turn rotates (indexes) the rotating carousel to the desired location. Angular position of the rotating carousel is monitored via position sensors and CECS. Therefore, at any given time, the CECS recognizes the location of each CM container. It can therefore determine by what angle the rotating carousel should be rotated in order to spike a specific CM container.

Upon the user opening the door of a temperature-controlled chamber, a sensor is triggered with feedback to the CECS. The CECS then disengages (mechanically, electrically, electronically, or otherwise) the carousel drive system such that the rotating carousel can no longer be automatically rotated. This then allows the user to "Free-Wheel" the rotating carousel, providing a means for the user to easily rotate the rotating carousel to access each individual CM container in the quickest manner possible.

Figure 11:
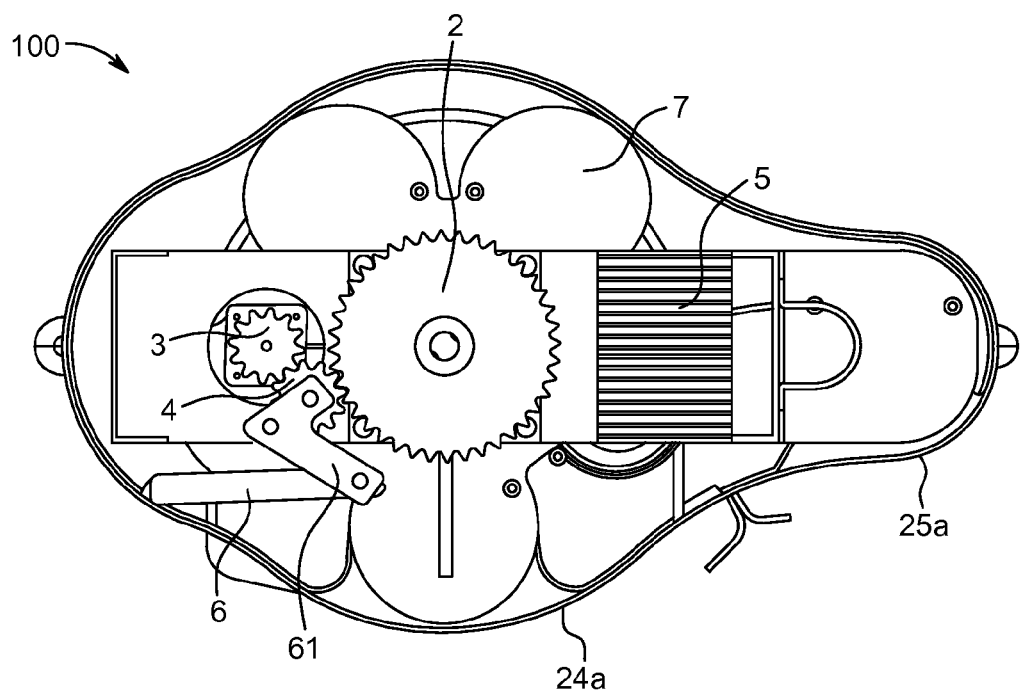
FIG. 11 is a first top view of a fluid management device

In one embodiment as shown in FIGS. 11, 12 and 13 the rotation from the motor is transmitted via motor gear 2, and idler gear 4 to main gear 2. The idler gear 4 is mounted to the first end of an attachment 61 which is pivoted, the second end of the attachment being movably connected to a an idler pin 6. The idler pin 6 being connected to the door of a temperature-controlled chamber. Upon opening the door of a temperature-controlled chamber as shown in FIG. 12, the idler pin 6 moves with the door and rotates the attachment 61 such that the idler gear 4 disengages from the motor gear 3 and the main gear 2.

Containers adapted to be used with the FMD, so-called approved containers, have an RFID tag (or other data storage means) attached to them. This allows the CECS to recognise at what time and in what location a container is replenished via interrogation with an RFID reader (or reader corresponding to the other data storage means) connected to the CECS. It also allows the CECS to ascertain if a non-approved container is placed in one of the container holders through interrogation of the RFID tag. If no RFID tag is present on the container, the CECS will recognise this upon trying to interrogate the container as no communication will be achieved. Should this be the case, the CECS will action a visual and/or audible error feedback to the user and then lock the relevant container location out from use so that it cannot be spiked. This is an important safety feature to ensure that only the correct fluids and approved containers are stored within the FMD for supply to the CM injector.

Likewise, an RFID tag is also attached to each FTS. The CECS is then able to interrogate each FTS presented to ensure it is approved for use.

Further once a spike of an FTS is spiked into a container septum the CECS logs the FTS as used and begins a countdown of a prescribed time which is the recommended in-use time for a spike. After the recommended in-use time for the spike, i.e. 24 hours, has elapsed the CECS then actions an error feedback via either visual or audible means to alert the user that the FTS must be replaced before further use of the FMS can occur.

Data stored on the RFID tag of each container such as the manufacturing date, fluid formulation, etc. is able to be interrogated and stored via the RFID reader and the CECS.

This data can then be transferred to the CM injector or saved onto mobile storage means (i.e. USB stick). This feature improves traceability.

Once a CM container has been spiked, a countdown timer is activated via the CECS and the respective CM container is logged by the CECS as having been spiked. After the recommended in-use time for the CM container has elapsed, and assuming the respective CM container is not yet defined as "Empty", the CECS locks the respective CM out and communicates with the automated spiking system to de-spike said CM container. As the unique code stored on the RFID tag of the CM container is logged in the CECS as used, and/or has elapsed past the defined useful life when spiked, the user is then prevented from both re-using the CM container and from replenishing that CM container within either temperature-controlled chamber at a later date.

In one embodiment information relevant to the CM injector (fluid supply levels/volume remaining, temperature) are displayed on the main user interface screen of the CM injector. This is achieved via direct data transfer between the FMD and CM injector. Information such as the temperature, which containers are empty/over the recommended in-use time, etc for each temperature-controlled chamber is intended to be displayed via LED's or display screen on the FMD. This feature allows the user to directly monitor fluid levels within the FMD with respect to the relevant chamber. A viewing window is also positioned on each of the chamber doors as a secondary means for the user to visually check fluid levels and for which containers require replenishment. The chamber doors allow the user access to replenish fluid supplies, provided a container within the chamber is not spiked at the time. Once a door on a temperature-controlled chamber is opened the carousel drive system is disengaged to prevent the rotating carousel from being automatically driven whilst the user replenishes supplies. The disengagement of the carousel drive system also allows the rotating carousel to free-wheel such that the user can easily rotate the rotating carousel to access each individual container in the quickest manner. Upon closing the door of the temperature-controlled chamber the carousel drive system is re-engaged in order to automatically drive the rotating carousel for use.

2-way communication between the FMS and the CM injector is achieved through a proprietary software communication platform. This enables the user to control and observe several functions of the FMD from the CM injector interface directly. Data transferral between the FMD and CM injector may be achieved through several transference means including, but not limited to, the following:

Wired cable—USB, LAN, or otherwise
Bluetooth
Wireless Network

One manually removable drip tray 13 is positioned beneath the rotating carousel and above the automated spiking system of each temperature-controlled chamber such that any CM fluid spillage from previously spiked CM container septums is captured within the confines of the machine.

In the embodiment of the FMS described in this example, it is possible for the CECS to recognise the locations of each container within the FMD, how long they have been sitting within the FMD, whether or not they have been spiked before, and whether or not the fluid in a specific container is past its useful life. This, in principle, removes safety concerns such as the user re-spiking a used or useful-life-elapsed container.

The FMS according to the second exemplary embodiment described herein is adapted to automatically supply pre-heated contrast media (CM) and pre-heated saline to a CM injector for injection into a patient from a container filled with CM (CM container) or a container filled with saline (Saline container).

Figure 15:
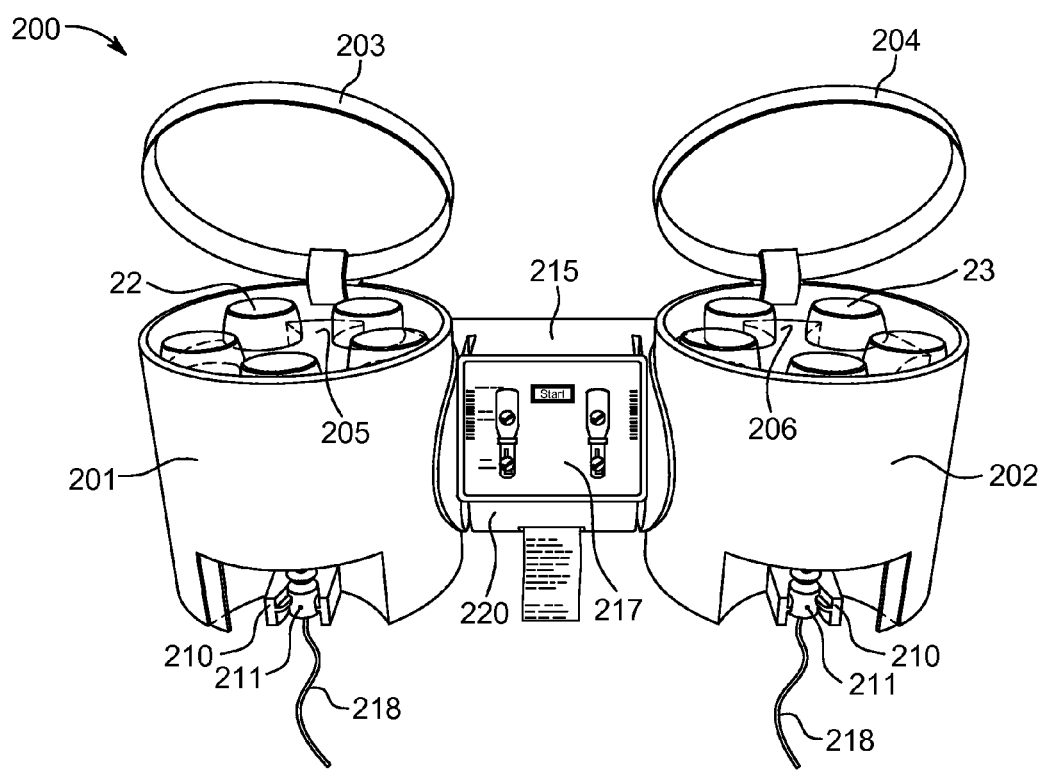
FIG. 15 is first perspective view of a second embodiment of the fluid management device
Figure 16:
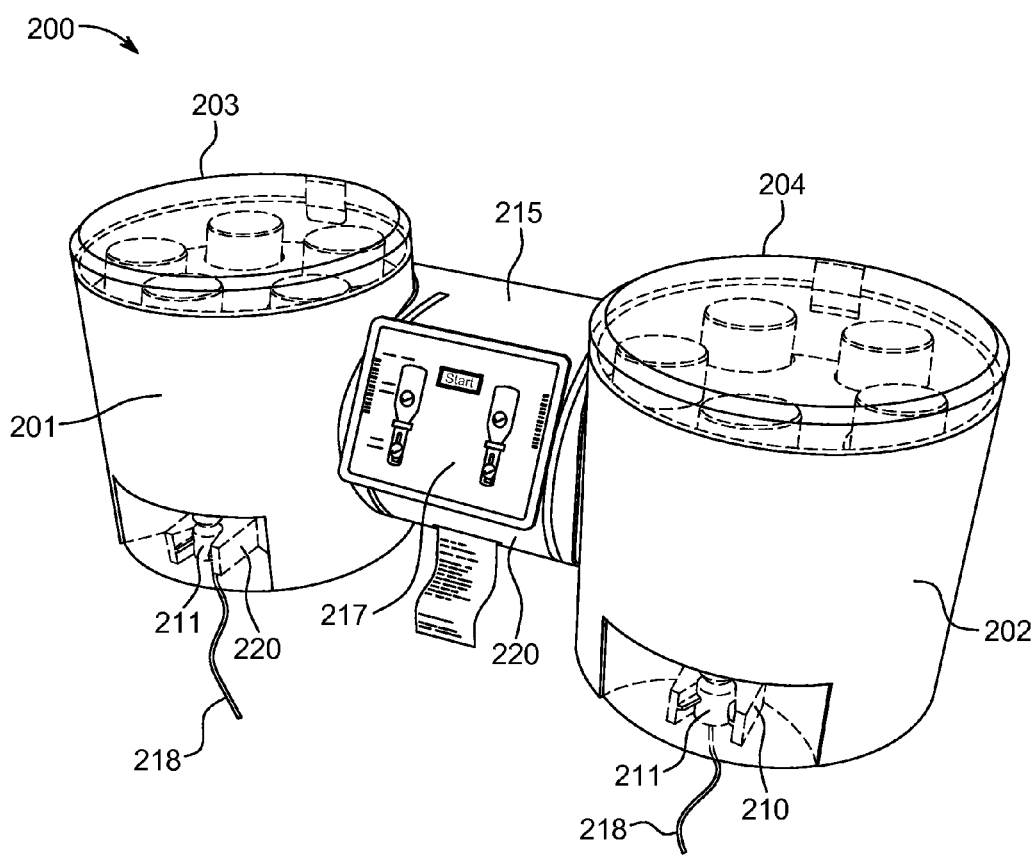
FIG. 16 is second perspective view of a second embodiment of the fluid management device

In FIGS. 15 and 16 a second embodiment of a FMD is shown. The FMD 200 of this embodiment comprises two chambers 201 and 202 attached to a chassis framework. Both chambers 201, 202 are temperature-controlled. Each chamber 201, 202 houses a rotating carousel 205, 206. Five container holders are mounted on each rotating carousel 205, 206 for holding up to five CM containers 22 and up to five Saline containers 23. Each chamber 201, 202 has a lid 203, 204 and is adapted to be loaded from the top. Between both chambers 201, 202 a housing 215 for a CECS is mounted to the chassis framework together with a display 217 and a printer 220.

A vertically moveable the spike holder 210 is mounted vertically to the chassis framework below each of the two chambers 201 and 202. Said automated spiking system is positioned and orientated such that each spike holder 210 is adapted to axially align a spike 211 with the axis of the container 22, 23 that is to be spiked. Tubing 218 connected to each spike 211 is adapted to transfer the fluid from the spiked container to the CM injector.

The functional description of the first exemplary embodiment described above applies mutatis mutandis to this second exemplary embodiment.

ABBREVIATIONS AND REFERENCE NUMERALS

FMS Fluid Management System
FMD, 100 Fluid Management Device
FTS Fluid Transfer System
CM contrast media
CECS central electronic control system
1 ceiling arm attachment
31 bail
5 heater for temperature-controlled chamber
14 chassis framework
2 main gear
3 motor gear
4 idler gear
6 idler pin
61 attachment
20a,b temperature-controlled chamber
21a,b non-temperature-controlled chamber
22 CM Container
23 Saline container
24a,b door of temperature-controlled chamber
25a,b door of non-temperature-controlled chamber
26 window
27 carousel drive shaft
7 plate (carousel)
18 plate (saline holder)
8 wire container rack
28 clip
13 drip tray
15 tubing to top chamber spike
16 tubing to lower chamber spike
17 Y-connector
18 tubing to CM injector
9 linear slide
10 spike holder
11 spike
12 automated spiking system
43 sheath for spike 41 base
42 top
44 hole
45 guide notch
54 pin
55 slide rail
200 FMD—second embodiment
201 first temperature-controlled chamber
202 second temperature-controlled chamber
203 lid for first temperature-controlled chamber
204 lid for second temperature-controlled chamber
205, 206 rotating carousel
210 spike holder
211 spike
215 housing for CECS
217 display
220 printer

What is claimed is:

1. A fluid management device for automatic supply of a medical fluid to a fluid injector for injection into a patient, the device comprising:
   at least one rotating carousel with a vertical axis of rotation;
   at least two container holders each configured for holding a separate corresponding container, wherein the at least two container holders are fixedly attached to the at least one rotating carousel prior to, during, and after spiking, and during supply of the medical fluid to the fluid injector for injection into the patient, wherein each of the at least two container holders positions the corresponding container vertically with a septum covered end of a neck of the corresponding container facing downwards prior to, during, and after spiking, and during supply of the medical fluid to the fluid injector for injection into the patient;
   a spike holder mounted below the at least one rotating carousel and oriented such that the spike holder axially aligns a spike with an axis of the corresponding container loaded into the container holder and being held in a spiking position, wherein the spike holder is moveably mounted to a linear slide allowing the spike holder to slide upwards in a vertical direction to spike the corresponding container and to slide downwards in the vertical direction for de-spiking the corresponding container and wherein the spike holder is driven by an automated spiking system; and
   a central electronic control system adapted to communicate with the automated spiking system, wherein the central electronic control system comprises a timer that once the corresponding container has been spiked can determine if the corresponding container has exceeded a maximum in-use time, determine if the spike has exceeded a maximum in-use time, or combinations thereof.

2. The fluid management device of claim 1, comprising two rotating carousels.

3. The fluid management device of claim 2, wherein each rotating carousel is mounted in a separate chamber.

4. The fluid management device of claim 3, wherein all of the separate chambers are mounted to a chassis framework.

5. The fluid management device of claim 3, wherein at least one of the separate chambers is temperature-controlled.

6. The fluid management device of claim 3, wherein each of the separate chambers can be accessed by an individual hinged lid or door.

7. The fluid management device of claim 1, further comprising one or more container holders that are not attached to the at least one rotating carousel.

8. The fluid management device of claim 7, wherein each of the one or more container holders that is not attached to the at least one rotating carousel is mounted in a separate chamber.

9. The fluid management device of claim 8, wherein all of the separate chambers are mounted to a chassis framework.

10. The fluid management device of claim 8, wherein at least one of the separate chambers is temperature controlled.

11. The fluid management device of claim 8, wherein each of the separate chambers can be accessed by an individual hinged lid or door.

12. The fluid management device of claim 1, comprising two rotating carousels and two container holders that are not attached to the two rotating carousels.

13. The fluid management device of claim 1, wherein all of the at least two container holders attached to the at least one rotating carousel are adapted to hold containers of equal size, or alternatively some of the at least two container holders are adapted to hold containers of different size than other of the at least two container holders.

14. The fluid management device of claim 13, wherein one of the at least two container holders is adapted to hold a container that is smaller in size than other containers.

15. The fluid management device of claim 1, wherein the central electronic control system is adapted to control rotation of the at least one rotating carousel and movement of the spike holder.

16. A fluid management system for automatically supplying a medical fluid for injection into a patient, the system comprising:
   the fluid injector and the fluid management device of claim 1, and a fluid transfer system, wherein the fluid transfer system comprises at least a first transfer tubing comprising two tubes, with at least two first ends, each of the at least two first ends connected to each of at least two spikes, and at least two second ends, each of the at least two second ends corresponding to each of the at least two first ends;
   a manifold having at least two input openings and one output opening, the at least two second ends of the first transfer tubing being connected to the at least two input openings of the manifold;
   a second transfer tubing having a first end and a second end, the first end of the second transfer tubing being connected to the output opening of the manifold; and
   a valve mounted between each of the at least two first ends and the at least two second ends of the first transfer tubing.

17. The fluid management device of claim 1, wherein the central electronic control system is further adapted to monitor a fluid level/volume of the container once the container has been spiked.

18. The fluid management device of claim 17, wherein the fluid level/volume of the container is monitored with fluid level/volume sensors.

* * * * *

UNITED STATES PATENT AND TRADEMARK OFFICE
CERTIFICATE OF CORRECTION

| | |
|---|---|
| PATENT NO. | : 9,555,189 B2 |
| APPLICATION NO. | : 13/512565 |
| DATED | : January 31, 2017 |
| INVENTOR(S) | : Reisinger et al. |

It is certified that error appears in the above-identified patent and that said Letters Patent is hereby corrected as shown below:

In the Specification

In Column 3, Line 23, delete "housing" and insert -- housing of --, therefor.
In Column 7, Line 62, delete "container holder 8" and insert -- container holder 110 --, therefor.
In Column 8, Line 27, delete "motor gear 2," and insert -- motor gear 3, --, therefor.
In Column 8, Line 30, delete "a an" and insert -- an --, therefor.

Signed and Sealed this
Second Day of May, 2017

Michelle K. Lee
*Director of the United States Patent and Trademark Office*